US00PP14675P29

(12) United States Plant Patent
Uchneat

(10) Patent No.: US PP14,675 P2
(45) Date of Patent: Apr. 6, 2004

(54) DOUBLE IMPATIENS PLANT NAMED 'BALFIESPRAY'

(50) Latin Name: *Impatiens walleriana*
Varietal Denomination: Balfiespray

(75) Inventor: Michael S. Uchneat, St. Charles, IL (US)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/359,747

(22) Filed: Feb. 6, 2003

(51) Int. Cl.[7] ..... A10H 5/00
(52) U.S. Cl. ..... Plt./317
(58) Field of Search ..... Plt./317

*Primary Examiner*—Bruce R. Campell
*Assistant Examiner*—June Hwu
(74) *Attorney, Agent, or Firm*—C. A. Whealy

(57) ABSTRACT

A new and distinct cultivar of Double Impatiens plant named 'Balfiespray', characterized by its upright, outwardly spreading and mounded plant habit; freely branching growth habit; dark green-colored leaves; and red purple and light pink bi-colored flowers that are fully double and positioned above the foliage.

1 Drawing Sheet

Botanical classification/cultivar designation: *Impatiens walleriana* cultivar Balfiespray.

BACKGROUND OF THE INVENTION

The present Invention relates to a new and distinct cultivar of Double Impatiens plant, botanically known as *Impatiens walleriana*, and hereinafter referred to by the name 'Balfiespray'.

The new Double Impatiens is a product of a planned breeding program conducted by the Inventor in Elburn, Ill. The objective of the breeding program was to develop new Double Impatiens cultivars with fully double flowers, freely branching growth habit and attractive flower and foliage coloration.

The new Impatiens originated from a cross-pollination made by the Inventor in February, 2000, of a proprietary *Impatiens walleriana* selection identified as code number 3306c-1, not patented, as the female, or seed parent, with a proprietary *Impatiens walleriana* selection identified as code number 10997, not patented, as the male, or pollen parent. The cultivar Balfiespray was discovered and selected by the Inventor as a flowering plant within the progeny of the stated cross-pollination in a controlled environment in Elburn, Ill.

Asexual reproduction of the new cultivar by terminal cuttings taken at Elburn, Ill. since April, 2000, has shown that the unique features of this new Impatiens are stable and reproduced true to type in successive generations of asexual reproduction.

SUMMARY OF THE INVENTION

The following traits have been repeatedly observed and are determined to be the unique characteristics of 'Balfiespray'. These characteristics in combination distinguish 'Balfiespray' as a new and distinct Double Impatiens cultivar:

1. Upright, outwardly spreading and mounded plant habit.
2. Freely branching growth habit.
3. Dark green-colored leaves.

4. Red purple and light pink bi-colored flowers that are fully double and positioned above and beyond the foliage.

Plants of the new Impatiens differ primarily from plants of the parent selections in flower color.

The new Impatiens can be compared to the *Impatiens walleriana* cultivar Sparkler Rose, disclosed in U.S. Plant Pat. No. 9,603. However, in side-by-side comparisons conducted in West Chicago, Ill., plants of the new Impatiens differed from plants of the cultivar Sparkler Rose in the following characteristics:

1. Plants of the new Impatiens were more compact than plants of the cultivar Sparkler Rose.
2. Plants of the new Impatiens were more freely flowering than plants of the cultivar Sparkler Rose.
3. Plants of the new Impatiens and the cultivar Sparkler Rose differed slightly in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Impatiens.

The photograph at the top of the sheet comprises a side perspective view of a flowering plant of 'Balfiespray'.

The photograph at the bottom of the sheet is close-up view of a typical flower and leaves of 'Balfiespray'.

DETAILED BOTANICAL DESCRIPTION

The cultivar Balfiespray has not been observed under all possible environmental conditions. The phenotype may vary somewhat with variations in environment such as temperature and light intensity without, however, any variance in genotype. The aforementioned photographs and following observations and measurements describe plants grown in West Chicago, Ill., under commercial practice in a polycarbonate-covered greenhouse with day temperatures ranging from 18 to 24° C., night temperatures ranging from 10 to 17° C. and light levels ranging from 4,000 to 6,000 footcandles. Rooted young plants were planted in 10-cm containers and had been growing for about eight weeks when the photographs and the description were taken.

In the following description, color references are made to The Royal Horticultural Society Colour Chart, 2001 Edition, except where general terms of ordinary dictionary significance are used.

Botanical classification: *Impatiens walleriana* cultivar Balfiespray.

Parentage:

*Female parent.*—Proprietary *Impatiens walleriana* selection identified as code number 3306c-1, not patented.

*Male parent.*—Proprietary *Impatiens walleriana* selection identified as code number 10997, not patented.

Propagation:

*Type cutting.*—Terminal cuttings.

*Time to initiate roots.*—About 7 days at 18° C.

*Time to produce a rooted young plant.*—About 21 days at 18° C.

*Root description.*—Fibrous.

*Rooting habit.*—Freely branching.

Plant description:

*General appearance.*—Upright, outwardly spreading and mounded plant habit.

*Growth and branching habit.*—Moderately vigorous and freely-branching growth habit with about three or four basal branches; lateral branches potentially forming at every node; dense and bushy growth. Pinching, that is, removal of the terminal apices, is not required, but enhances branching.

*Plant height.*—About 16.6 cm.

*Plant diameter or spread.*—About 32.6 cm.

*Lateral branches.*—Length: About 13.7 cm. Diameter: About 7 mm. Internode length: About 2.3 cm. Texture: Smooth, glabrous. Color: 146C overlain with 183A.

*Foliage description.*—Arrangement: Opposite, simple. Length: About 4 cm. Width: About 2.4 cm. Shape: Ovate. Apex: Acuminate. Base: Attenuate. Margin: Crenate with ciliation. Texture, upper and lower surfaces: Smooth, glabrous. Venation pattern: Pinnate. Color: Developing and fully expanded foliage, upper surface: 147A. Developing and fully expanded foliage, lower surface: 147B with random blotches, 183D. Venation, upper surface: 148C. Venation, lower surface: 146B. Petiole: Length: About 1.2 cm. Diameter: About 2.5 mm. Texture, upper and lower surfaces: Smooth, glabrous. Color: 145C.

Flower description:

*Flower type and habit.*—Numerous and consistently double flowers. Flower buds open similar to a rose in fullness; flowers rounded in shape. Flowers arise from leaf axils. Freely flowering, usually about four flowers and flower buds per lateral branch. Flowers positioned above the foliage and typically face upright or outward. Flowers last about five to seven days under greenhouse conditions. Flowers not persistent. Flowers not fragrant.

*Natural flowering season.*—Flowering is continuous through the spring and summer in West Chicago, Ill.

*Flower size.*—Diameter: About 4.4 cm. Depth: About 2.6 cm.

*Flower buds* (*at stage of showing color*).—Length: About 1.4 cm. Diameter: About 1 cm. Shape: Ovoid. Color: 55A.

*Petals.*—Quantity/arrangement: About 24 per flower; imbricate. Length, outermost petals: About 2.4 cm. Width, outermost petals: About 1.5 cm. Length, innermost petals: About 1.3 cm. Width, innermost petals: About 1 cm. Shape: Obovate. Apex: Emarginate. Base: Attenuate. Margin: Entire. Texture, upper and lower surfaces: Smooth. Color: When opening and fully opened, upper surface: 57A; midrib, varying from 68B to lighter than 68D; color becoming closer to darker than 57A with development. When opening and fully opened, lower surface: 43D; midrib, 155D.

*Sepals.*—Quantity/arrangement: Five in a single whorl; one modified into an elongated spur. Calyx length: About 1 cm. Calyx diameter: About 1 cm. Shape: Elliptic. Apex: Acute. Margin: Entire. Texture, upper and lower surfaces: Smooth, glabrous. Color, upper and lower surfaces: Close to 144A. Spur length: About 3.3 cm. Spur diameter: At flower, about 1.6 mm; at apex, less than 1 mm. Spur color: 145C overlain with 183D.

*Peduncles.*—Length: About 1.7 cm. Diameter: About 1.1 mm. Angle: Acute. Strength: Strong. Texture: Smooth, glabrous. Color: 145B.

*Reproductive organs.*—None observed.

*Seed/fruit.*—None observed.

Disease/pest resistance: Plants of the new Impatiens have not been observed to be resistant to pathogens and pests common to Impatiens.

It is claimed:

1. A new and distinct cultivar of Double Impatiens plant named 'Balfiespray', as illustrated and described.

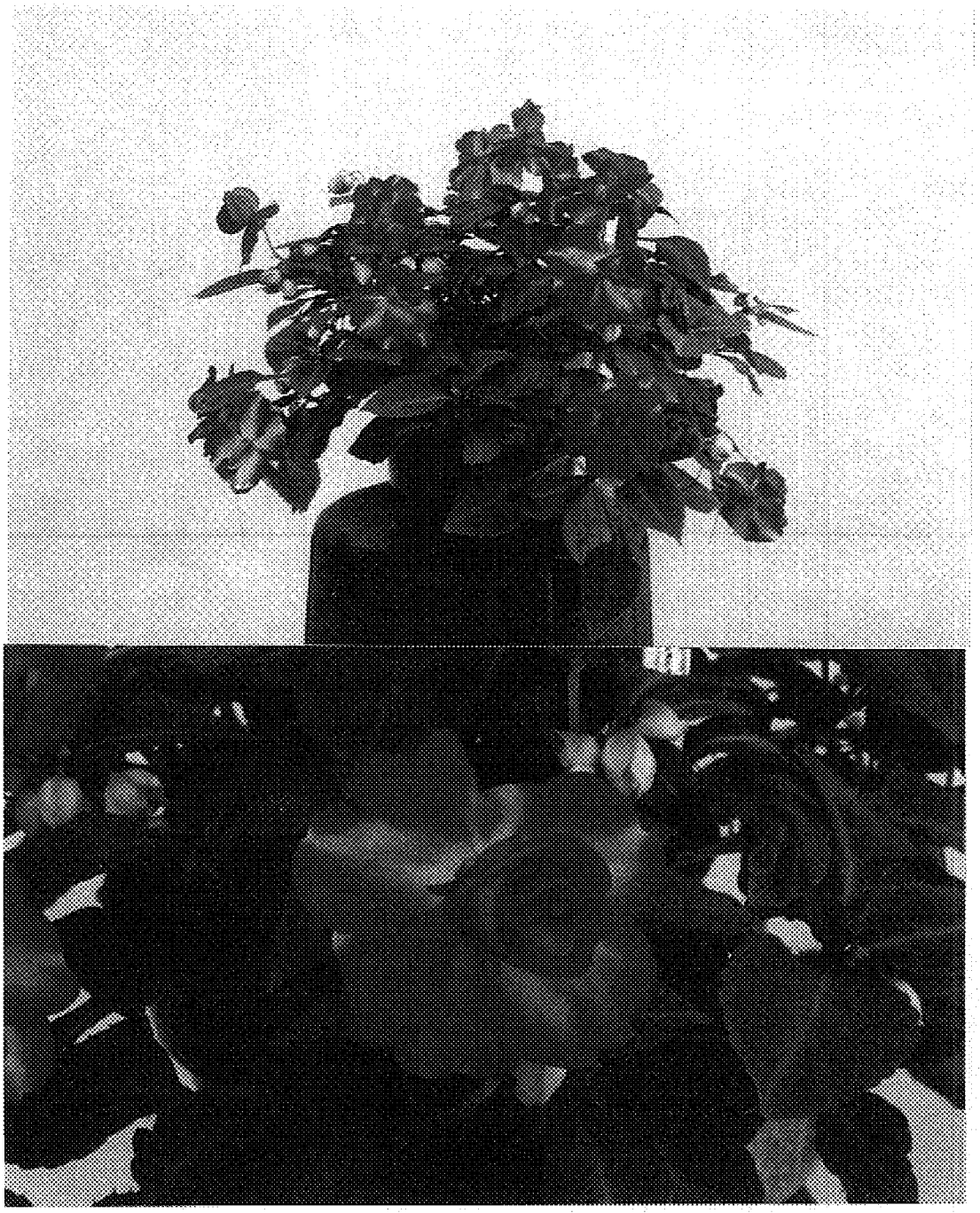

* * * * *